(12) United States Patent
Kobayashi

(10) Patent No.: US 11,457,797 B2
(45) Date of Patent: Oct. 4, 2022

(54) ENDOSCOPIC DEVICE

(71) Applicant: Sony Olympus Medical Solutions Inc., Tokyo (JP)

(72) Inventor: Motoaki Kobayashi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 822 days.

(21) Appl. No.: 16/149,268

(22) Filed: Oct. 2, 2018

(65) Prior Publication Data

US 2019/0125168 A1 May 2, 2019

(30) Foreign Application Priority Data

Oct. 27, 2017 (JP) .............................. JP2017-208494

(51) Int. Cl.
| | |
|---|---|
| *A61B 1/00* | (2006.01) |
| *H04N 5/232* | (2006.01) |
| *H04N 5/225* | (2006.01) |
| *A61B 1/04* | (2006.01) |
| *G02B 23/24* | (2006.01) |

(52) U.S. Cl.
CPC ...... *A61B 1/00105* (2013.01); *A61B 1/00009* (2013.01); *A61B 1/0011* (2013.01); *A61B 1/00057* (2013.01); *A61B 1/00096* (2013.01); *A61B 1/00101* (2013.01); *A61B 1/00128* (2013.01); *A61B 1/00137* (2013.01); *A61B 1/00186* (2013.01); *A61B 1/042* (2013.01); *G02B 23/2484* (2013.01); *H04N 5/2252* (2013.01); *H04N 5/2253* (2013.01); *H04N 5/2254* (2013.01); *H04N 5/232* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 5,609,561 | A * | 3/1997 | Uehara | A61B 1/042 348/75 |
| 5,879,284 | A * | 3/1999 | Tsujita | A61B 1/043 600/109 |
| 6,280,378 | B1 * | 8/2001 | Kazuhiro | A61B 1/0638 348/65 |
| 9,107,573 | B2 * | 8/2015 | Birnkrant | A61B 1/00114 |
| 2007/0213586 | A1 * | 9/2007 | Hirose | A61B 1/00105 600/112 |
| 2008/0108869 | A1 * | 5/2008 | Sanders | A61B 1/00103 600/109 |

(Continued)

FOREIGN PATENT DOCUMENTS

| | | |
|---|---|---|
| JP | H0228889 A | 1/1990 |
| JP | 2000139817 A | 5/2000 |

(Continued)

*Primary Examiner* — Timothy J Neal
(74) *Attorney, Agent, or Firm* — Xsensus LLP

(57) ABSTRACT

A disclosed endoscopic device includes a front cabinet unit including an optical system provided with a phase modulation element which modulates a space distribution of a phase of light; and a rear cabinet unit detachably connected to the front cabinet unit, the rear cabinet unit including an imaging unit which receives light transmitted through the optical system of the front cabinet unit, and converts the light into an electrical signal.

21 Claims, 9 Drawing Sheets

(56) References Cited

U.S. PATENT DOCUMENTS

| | | | | |
|---|---|---|---|---|
| 2008/0195128 | A1* | 8/2008 | Orbay | A61B 1/313 606/170 |
| 2016/0131900 | A1* | 5/2016 | Pretorius | G02B 13/0095 359/368 |

FOREIGN PATENT DOCUMENTS

| | | | |
|---|---|---|---|
| JP | 2000275582 | A | 10/2000 |
| JP | 2000279369 | A | 10/2000 |
| JP | 2002136477 | A | 5/2002 |
| JP | 2014230788 | A | 12/2014 |
| JP | 2016-214660 | | 12/2016 |
| JP | 2017158764 | A | 9/2017 |
| WO | WO-2016121165 | A1 | 8/2016 |

* cited by examiner

ENDOSCOPIC DEVICE

CROSS-REFERENCE TO RELATED APPLICATION(S)

The present application claims priority to and incorporates by reference the entire contents of Japanese Patent Application No. 2017-208494 filed in Japan on Oct. 27, 2017.

BACKGROUND

The present disclosure relates to an endoscopic device.

In the related art, in the medical field or the industrial field, an endoscopic device observing the inside of a subject such as a person or a machine structure is known (for example, refer to JP 2016-214660 A). The endoscopic device described in JP 2016-214660 A, includes an endoscope which is inserted into the subject, and takes in a subject image of the inside of the subject from a distal end, an imaging device (an image sensor) which is provided in the endoscope, and which captures an image of the subject and outputs an image signal, a control device which processes the image signal, and generates a video signal for display, and a display device which displays an image based on the video signal. In JP 2016-214660 A, in the imaging device, an image sensor mounting portion on which the image sensor is mounted, is fixed to a lens unit forming an optical system.

SUMMARY

However, in JP 2016-214660 A, the image sensor mounting portion and the lens unit are integrally disposed, and thus, it is necessary to detach both of the image sensor mounting portion and the lens unit, for example, at the time of performing repair. In contrast, in a case where a casing retaining the image sensor mounting portion is separated from a casing retaining the lens unit, it is sufficient to disassemble only one casing, which is a repair target, and thus, the repair can be efficiently performed. However, when the casings are connected to each other after the repair, it is difficult to perform accurate positioning between the image sensor and the lens unit, and there is a case where a depth of field decreases according to the arrangement of the image sensor and the lens unit after the connection of the casings.

Therefore, there is a need for at least partially solving disadvantages stated above in the related art.

According to an embodiment of the present disclosure, an endoscopic device is provided which includes a front cabinet unit including an optical system provided with a phase modulation element which modulates a space distribution of a phase of light; and a rear cabinet unit detachably connected to the front cabinet unit, the rear cabinet unit including an imaging unit which receives light transmitted through the optical system of the front cabinet unit, and converts the light into an electrical signal.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Figure 1:
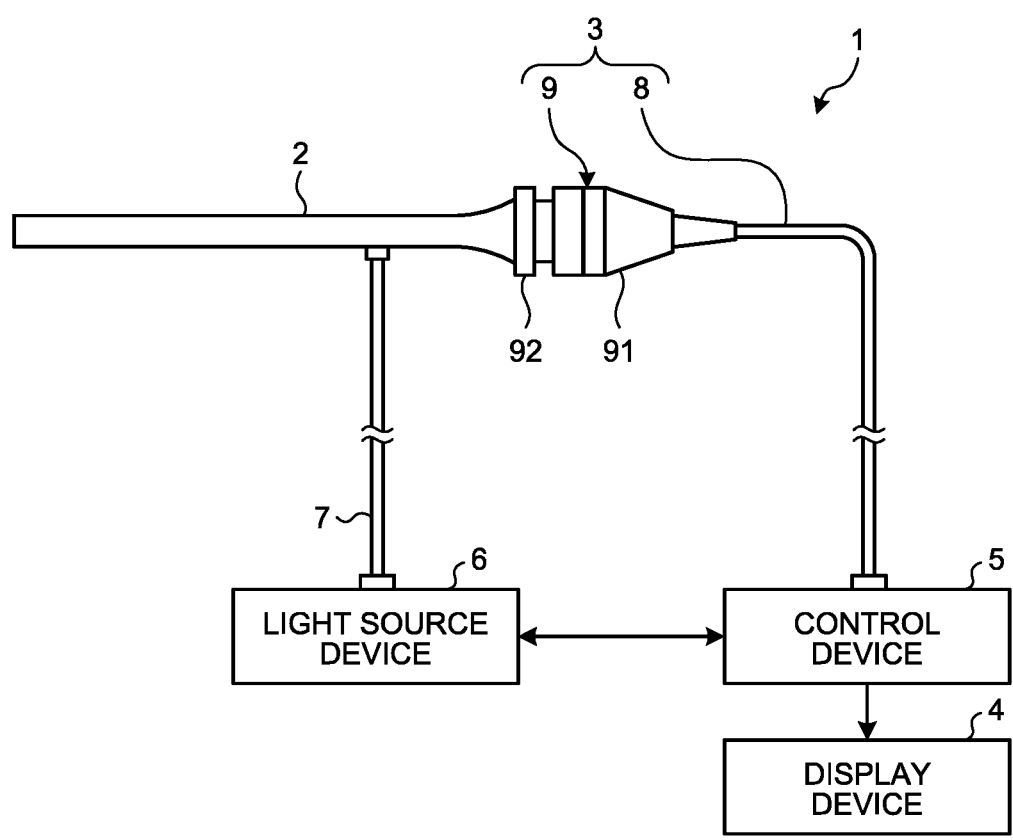
FIG. 1 is a diagram illustrating a schematic configuration of an endoscopic device according to one embodiment of the present disclosure.

Hereinafter, modes for carrying out the present disclosure (hereinafter, referred to as "embodiments") will be described. In the embodiments, a medical endoscopic device which images and displays an image in a subject such as a patient, will be described as one example of an endoscopic device according to the present disclosure. In addition, the present disclosure is not limited to the embodiments. Further, in the drawings, the same reference numerals are applied to the same constituents.

EMBODIMENTS

FIG. 1 is a diagram illustrating a schematic configuration of an endoscopic device 1 according to one embodiment of the present disclosure. The endoscopic device 1 is a device which is used in the medical field, and observes a subject in an observation target (in a living body) such as a person. As illustrated in FIG. 1, the endoscopic device 1 includes an endoscope 2, an imaging device 3, a display device 4, a control device 5 (an image processing device), and a light source device 6, and a medical image acquisition system is configured of the imaging device 3 and the control device 5.

One end of a light guide 7 is connected to the endoscope 2, and the light source device 6 supplies, for example, white illumination light for illuminating the inside of the living body to the one end of the light guide 7. The light guide 7 is detachably connected at the one end to the endoscope 2 and is detachably connected at the other end to the light source device 6. Then, the light guide 7 allows the light supplied from the light source device 6 to propagate from the other end through the one end, thereby to supply the light to the endoscope 2. Furthermore, in this embodiment, it is described that the white illumination light is emitted, but illumination light such as infrared light, or light of which a wavelength band is limited, may be used in other embodiments.

The imaging device 3 captures an image of a subject through the endoscope 2, and outputs the imaging result. As illustrated in FIG. 1, the imaging device 3 includes a transmission cable 8, which is a signal transmission unit, and a camera head 9. In this embodiment, a medical imaging device is configured of the transmission cable 8 and the camera head 9.

The endoscope 2 is rigid and has an elongated shape, and is inserted into the living body. In the endoscope 2, an optical system which is configured of one or a plurality of lenses and condenses the subject image, is disposed. The endoscope 2 emits the light supplied through the light guide 7 from a distal end, and irradiates the living body with the light. Then, the light emitted into the living body (the subject image) is condensed by an optical system in the endoscope 2.

The camera head 9 is detachably connected to a proximal end of the endoscope 2. Then, the camera head 9 captures an image of the subject which is condensed in the endoscope 2, and outputs an imaging signal according to the imaging, under the control of the control device 5. Furthermore, the detailed configuration of the camera head 9 will be described below.

One end of the transmission cable 8 is detachably connected to the control device 5 through a connector, and the other end is detachably connected to the camera head 9 through the connector. Specifically, the transmission cable 8 is a cable in which a plurality of electrical wirings (not illustrated) are disposed inside of an outer cover serving as the outermost layer. The plurality of electrical wirings are electrical wirings for respectively transmitting the imaging signal output from the camera head 9, a control signal output from the control device 5, a synchronization signal, a clock, and power, to the camera head 9.

The display device 4 displays an image which is generated by the control device 5, under the control of the control device 5. It is preferable that a display unit is greater than or equal to 55 inches in order to easily obtain a sense of immersion at the time of observation, but the display device 4 is not limited thereto.

The control device 5 processes the imaging signal input from the camera head 9 through the transmission cable 8, outputs the image signal to the display device 4, and generally controls the operation of the camera head 9 and the display device 4. The detailed configuration of the control device 5 will be described below.

Figure 2:
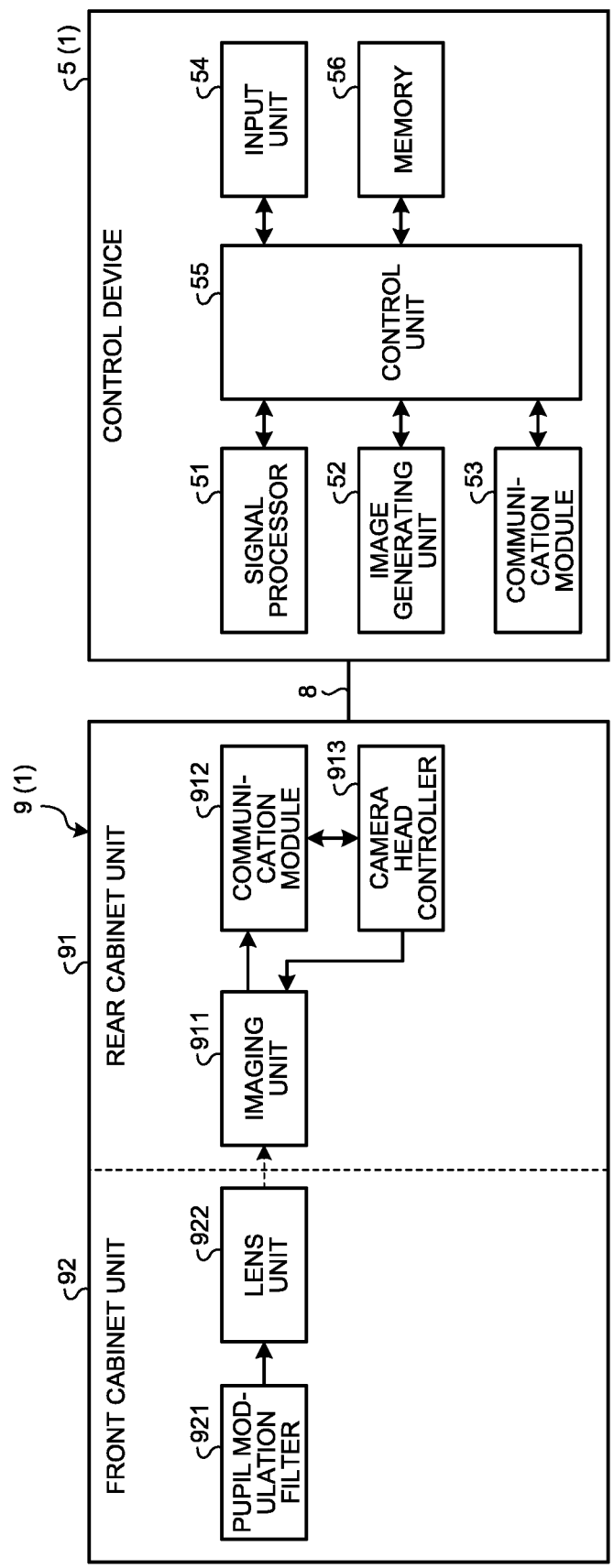
FIG. 2 is a block diagram illustrating a configuration of a camera head and a control device illustrated in FIG. 1.

Next, the configuration of the imaging device 3 and the control device 5 will be described. FIG. 2 is a block diagram illustrating the configurations of the camera head 9 and the control device 5. Furthermore, in FIG. 2, the connector detachably attaching the camera head 9 and the transmission cable 8 to each other is not illustrated.

Hereinafter, the configuration of the control device 5 and the configuration of the camera head 9 will be described in this order. Furthermore, hereinafter, a main part of the present disclosure will be mainly described, as the configuration of the control device 5. As illustrated in FIG. 2, the control device 5 includes a signal processor 51, an image generating unit 52, a communication module 53, an input unit 54, a control unit 55, and a memory 56. Furthermore, in the control device 5, a power supply unit (not illustrated) or the like, which generates a power source voltage for driving the control device 5 and the camera head 9, supplies the power source voltage to each unit of the control device 5, and supplies the power source voltage to the camera head 9 through the transmission cable 8, may be disposed.

The signal processor 51 performs noise removing, and signal processing such as analog-to-digital (A/D) conversion, as necessary, with respect to the imaging signal output by the camera head 9, and outputs a digitalized imaging signal (a pulse signal) to the image generating unit 52.

In addition, the signal processor 51 generates the synchronization signal of the imaging device 3 and the control device 5, and a clock signal. The synchronization signal (for example, a synchronization signal indicating an imaging timing of the camera head 9) with respect to the imaging device 3 or the clock signal (for example, a clock for serial communication) is transmitted to the imaging device 3 through a line (not illustrated), and the imaging device 3 is driven on the basis of the synchronization signal or the clock.

The image generating unit 52 generates an image signal for display, which is displayed on the display device 4, on the basis of the imaging signal input from the signal processor 51. The image generating unit 52 executes predetermined signal processing with respect to the imaging signal, and generates an image signal for display including the subject image. Here, the image generating unit 52 performs restoration processing with respect to a signal which is modulated by a pupil function phase distribution of a pupil modulation filter 921 described below, and generates a captured image for enlarging a depth of field, as the image processing, other than known image processing such as various image processes, for example, interpolation processing, color correction processing, color emphasizing processing, outline emphasizing processing, and the like. The image generating unit 52 performs restoration by performing digital processing using a point spread function (PSF). The image generating unit 52 outputs the generated image signal to the display device 4.

When the pupil modulation filter 921 is arranged in the camera head 9, and an image is generated on the basis of light transmitted through the pupil modulation filter 921, the image is generated by using the point spread function (PSF). With this, the depth of field is enlarged. Such a technology is generally referred to as wavefront coding (WFC).

The communication module 53 outputs a signal received from the control device 5 to the imaging device 3. The signal from the control device 5 includes a control signal transmitted from the control unit 55, described below. In addition, a signal from the imaging device 3 is output to the control device 5. That is, the communication module 53 is a relay device which collectively outputs signals from each of the units of the control device 5, to the imaging device 3, for example, according to parallel/serial conversion or the like, and distributively outputs the signal input from the imaging device 3 to each of the units of the control device 5, for example, according to serial/parallel conversion or the like.

The input unit 54 is realized by using a user interface such as a keyboard, a computer mouse, and a touch panel, and receives input of various information items.

The control unit 55 performs driving control of each configuration unit including the control device 5 and the camera head 9, and input/output control or the like of information with respect to each of the configuration units. The control unit 55 generates the control signal with reference to communication information data recorded in the memory 56 (for example, format information for communication and the like), and transmits the generated control signal to the imaging device 3 through the communication module 53. In addition, the control unit 55 outputs the control signal to the camera head 9 through the transmission cable 8.

The memory 56 is realized by using a semiconductor memory such as a flash memory or a dynamic random access memory (DRAM), and the communication information data (for example, the format information for communication and the like) is recorded in the memory 56. Furthermore, various programs or the like which are executed by the control unit 55, may be recorded in the memory 56.

Furthermore, the signal processor 51 may include an AF processor outputting a predetermined AF evaluation value of each frame on the basis of the imaging signal of input frame, and an AF calculator performing AF calculation processing such that a frame, a focus lens position, or the like, which is most suitable as a focusing position, is selected from the AF evaluation value of each of the frames from the AF processor.

The signal processor 51, the image generating unit 52, the communication module 53, and the control unit 55, described above, are realized by using a general-purpose processor such as a central processing unit (CPU) including an internal memory (not illustrated) in which a program is recorded, or a dedicated processor such as various calculation circuits executing a specific function such as an application specific integrated circuit (ASIC) or the like. In addition, the signal processor 51, the image generating unit 52, the communication module 53, and the control unit 55, described above, may be configured by using a field programmable gate array (FPGA: not illustrated), which is one type of programmable integrated circuit. Furthermore, in a case where the signal processor 51, the image generating unit 52, the communication module 53, and the control unit 55, described above, are configured of the FPGA, a memory storing configuration data may be provided, and the FPGA, which is a programmable integrated circuit, may be configured according to the configuration data read out from the memory.

Next, a main part of the present disclosure will be described, as the configuration of the camera head 9. As illustrated in FIG. 2, the camera head 9 includes a pupil modulation filter 921, a lens unit 922, an imaging unit 911, a communication module 912, and a camera head controller 913.

The pupil modulation filter 921 is a phase modulation element which is arranged in a position through which an optical axis of the camera head 9 passes, and an incident pupil position of the lens unit 922. The pupil modulation filter 921 is configured by using a phase plate, and forms a defocused intermediate image by changing the imaging characteristics of the endoscope 2. Specifically, the pupil modulation filter 921 forms the intermediate image by modulating a space distribution of the phase of the light. The intermediate image is an image which does not depend on displacement in a focal position.

The lens unit 922 is configured by using one or a plurality of lenses, and forms the subject image that has passed through the pupil modulation filter 921, on an imaging surface of an image sensor configuring the imaging unit 911. One or the plurality of lenses are arranged along the optical axis. Furthermore, in the lens unit 922, an insertable and removable optical filter (for example, a filter cutting infrared light) or the like may be disposed on the optical axis, in addition to an optical zoom mechanism and a focus mechanism.

The imaging unit 911 images the subject, under the control of the camera head controller 913. The imaging unit 911 is configured by using an image sensor which receives the subject image formed by the lens unit 922, and converts the subject image into an electrical signal. The image sensor is configured of a charge coupled device (CCD) image sensor or a complementary metal oxide semiconductor (CMOS) image sensor. In a case where the image sensor is a CCD, for example, a signal processor (not illustrated) which performs signal processing (A/D conversion or the like) with respect to the electrical signal (an analog signal) from the image sensor, and outputs the imaging signal, is mounted on a sensor chip or the like. In a case where the image sensor is a CMOS, for example, a signal processor which performs signal processing (A/D conversion or the like) with respect to an electrical signal (an analog signal) converted from the light, and outputs the imaging signal, is included in the image sensor. The imaging unit 911 outputs the generated electrical signal to the communication module 912.

The communication module 912 outputs the signal transmitted from the control device 5, to each unit in the camera head 9, such as the camera head controller 913. In addition, the communication module 912 converts information or the like relevant to the current state of the camera head 9, into a signal format according to a transmission system set in advance, and outputs the converted signal to the control device 5 through the transmission cable 8. That is, the communication module 912 is a relay device which distributively outputs the signal input from the control device 5 or the transmission cable 8, for example, to each of the units of the camera head 9, according to serial/parallel conversion or the like, and collectively outputs the signal output to the control device 5 or the transmission cable 8 from each of the units of the camera head 9, for example, according to parallel/serial conversion or the like.

The camera head controller 913 controls the operation of the entire camera head 9, according to a driving signal input through the transmission cable 8, an instruction signal output from an operating unit by a user operation with respect to the operating unit such as a switch, which is disposed by being exposed to an outer surface of the camera head 9, or the like. In addition, the camera head controller 913 outputs the information relevant to the current state of the camera head 9 to the control device 5 through the transmission cable 8.

Furthermore, the communication module 912 and the camera head controller 913, described above, are realized by using the general-purpose processor such as the CPU including the internal memory (not illustrated) in which the program is recorded, or the dedicated processor such as various calculation circuits executing the specific function of the ASIC or the like. In addition, the communication module 912 and the camera head controller 913, described above, may be configured by using the FPGA, which is one type of programmable integrated circuit. Furthermore, in a case where the communication module 912 and the camera head controller 913, described above, are configured of the FPGA, the memory storing the configuration data may be provided, and the FPGA, which is the programmable integrated circuit, may be configured according to configuration data read out from the memory.

Furthermore, a signal processor performing signal processing with respect to the imaging signal which is generated by the imaging unit 911, may be configured on the camera head 9 or the transmission cable 8. In addition, an imaging clock for driving the imaging unit 911 may be generated on the basis of a reference clock generated by an oscillator (not illustrated) disposed in the camera head 9, and may be output to the imaging unit 911, or timing signals of various processes in the imaging unit 911 and the camera head controller 913, may be generated on the basis of a synchronization signal input from the control device 5 through the transmission cable 8, and may be respectively output to the imaging unit 911 and the camera head controller 913. In addition, the camera head controller 913 may be disposed in the transmission cable 8 or the control device 5, rather than in the camera head 9.

Figure 3:
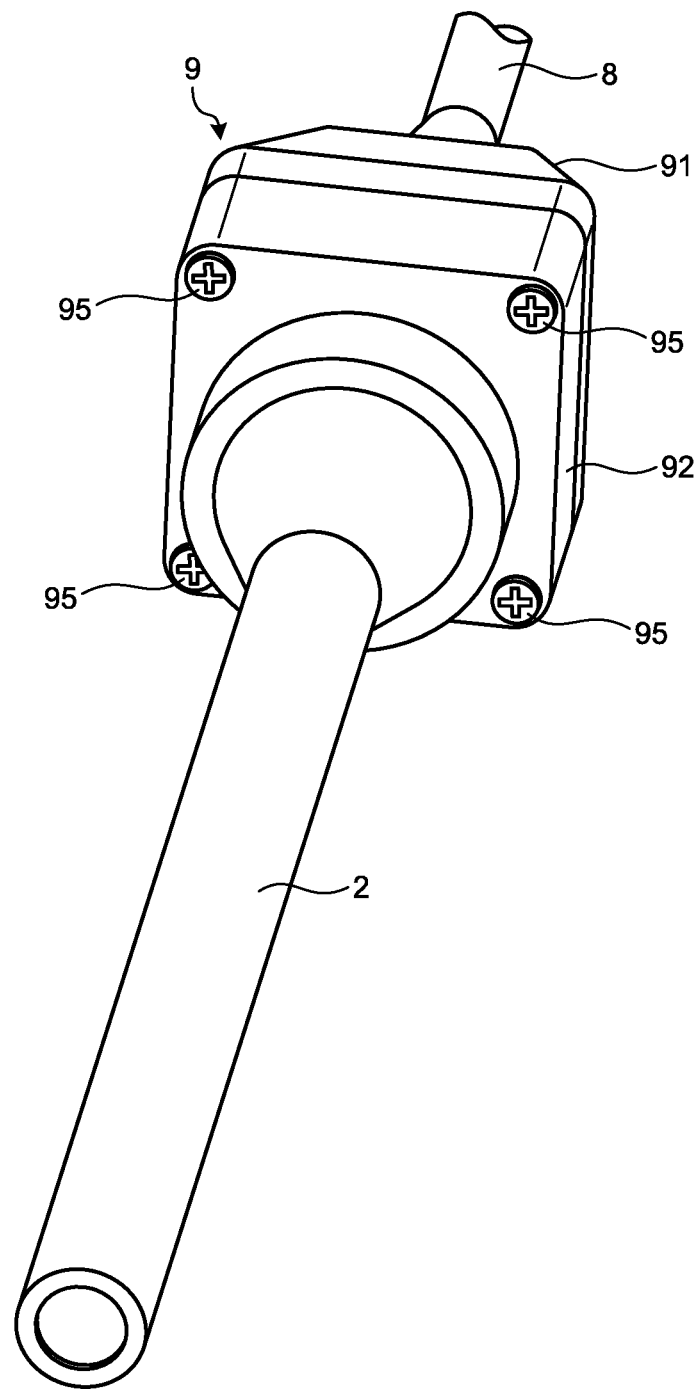
FIG. 3 is a perspective view illustrating the configuration of the camera head according to one embodiment of the present disclosure.
Figure 4:
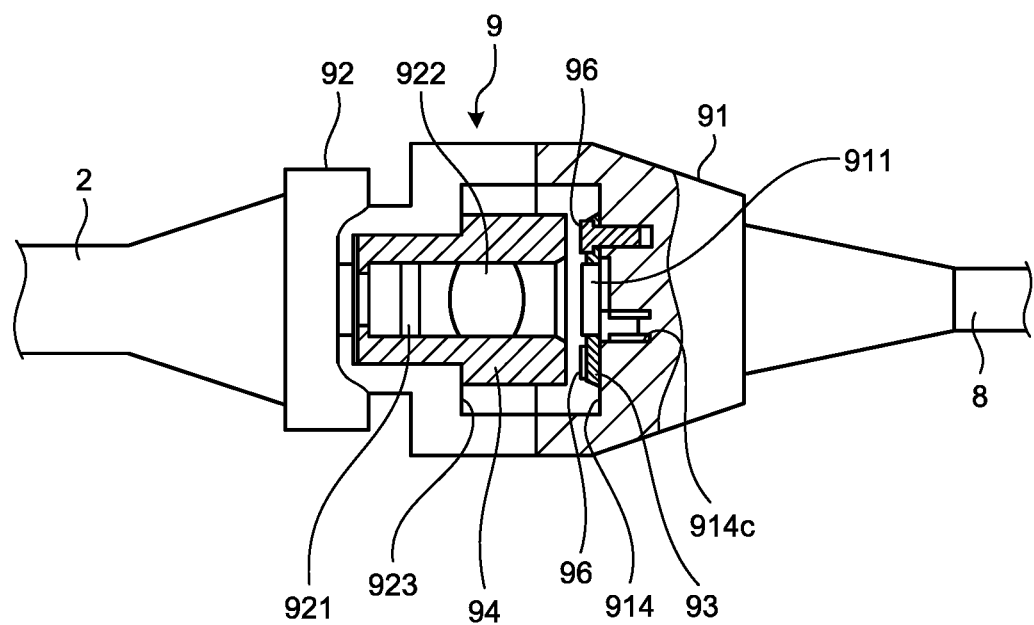
FIG. 4 is a partial sectional view illustrating the configuration of the camera head according to one embodiment of the present disclosure.

FIG. 3 is a perspective view illustrating the configuration of the camera head according to one embodiment of the present disclosure. FIG. 4 is a partial sectional view illustrating the configuration of the camera head according to one embodiment of the present disclosure. A casing of the camera head 9, retaining the pupil modulation filter 921, the lens unit 922, the imaging unit 911, the communication module 912, and the camera head controller 913, described above, is formed of a rear cabinet unit 91 and a front cabinet unit 92, which are detachably attached to each other.

Figure 5:
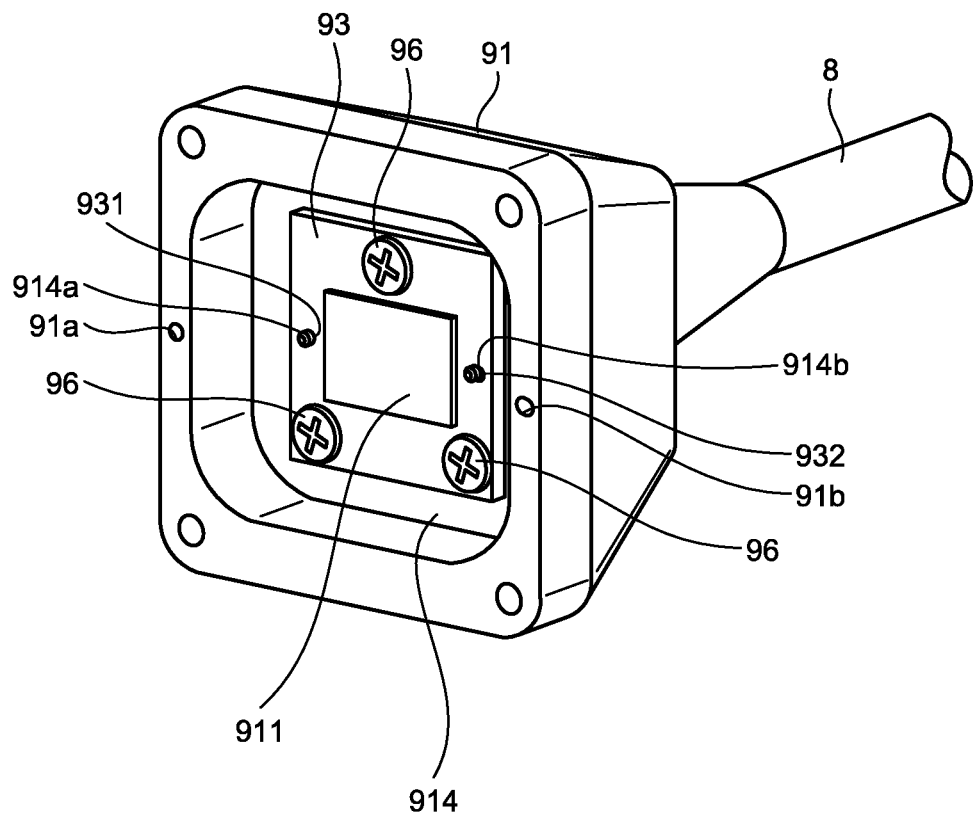
FIG. 5 is a perspective view illustrating a configuration of a main part of the camera head according to one embodiment of the present disclosure.
Figure 6:
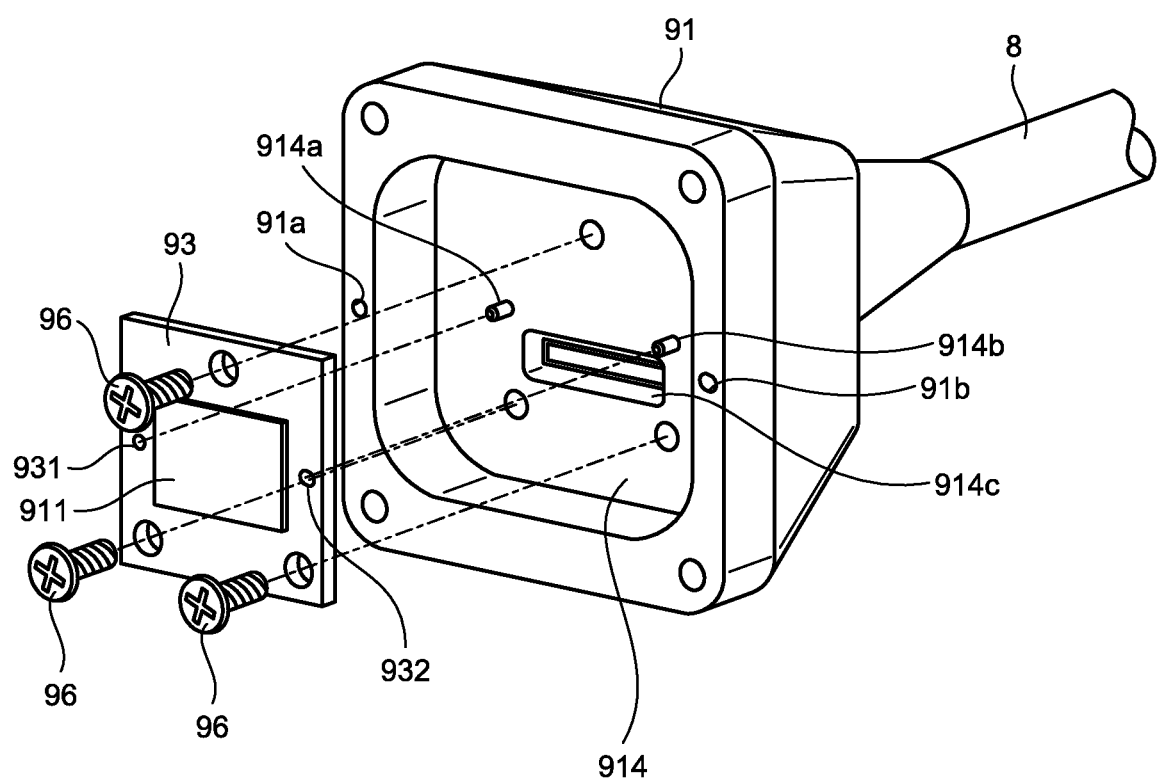
FIG. 6 is an exploded perspective view illustrating the configuration of the main part of the camera head according to one embodiment of the present disclosure.

FIG. 5 is a perspective view illustrating a configuration of a main part of the camera head according to one embodiment of the present disclosure, and is a diagram illustrating the configuration of the rear cabinet unit 91. FIG. 6 is an exploded perspective view illustrating the configuration of the main part of the camera head according to one embodiment of the present disclosure, and is an exploded perspective view of the rear cabinet unit 91. The rear cabinet unit 91 is connected to the transmission cable 8, and retains the imaging unit 911, the communication module 912, and the camera head controller 913 (FIG. 2). Specifically, an electrical system retaining unit 93, which is a package on which the image sensor configuring the imaging unit 911 is mounted, is attached to an attachment unit 914 formed in the rear cabinet unit 91. The electrical system retaining unit 93, for example, is screwed to the attachment unit 914 by a screw 96 (refer to FIG. 6). At this time, in the rear cabinet unit 91, positioning pins 914a and 914b formed in the attachment unit 914, are inserted into through holes 931 and 932, and thus, the electrical system retaining unit 93 is positioned and is prevented from being rotated. A slot 914c for being electrically connected to the electrical system retaining unit 93, of which a part is inserted into the attachment unit 914, is disposed in the electrical system retaining unit 93. The electrical system retaining unit 93 is electrically connected to the transmission cable 8 through the slot 914c. Here, an electrical circuit or the like configuring the communication module 912 or the camera head controller 913 is disposed between the slot 914c and the transmission cable 8. Furthermore, an electrical circuit configuring the communication module 912 or the camera head controller 913, may be disposed in a connector portion connected to the electrical system retaining unit 93 or the control device 5 of the transmission cable 8. In addition, the imaging unit 911 or the like may be mounted on a portion in which the rear cabinet unit 91 and the electrical system retaining unit 93 may be integrally molded.

Figure 7:
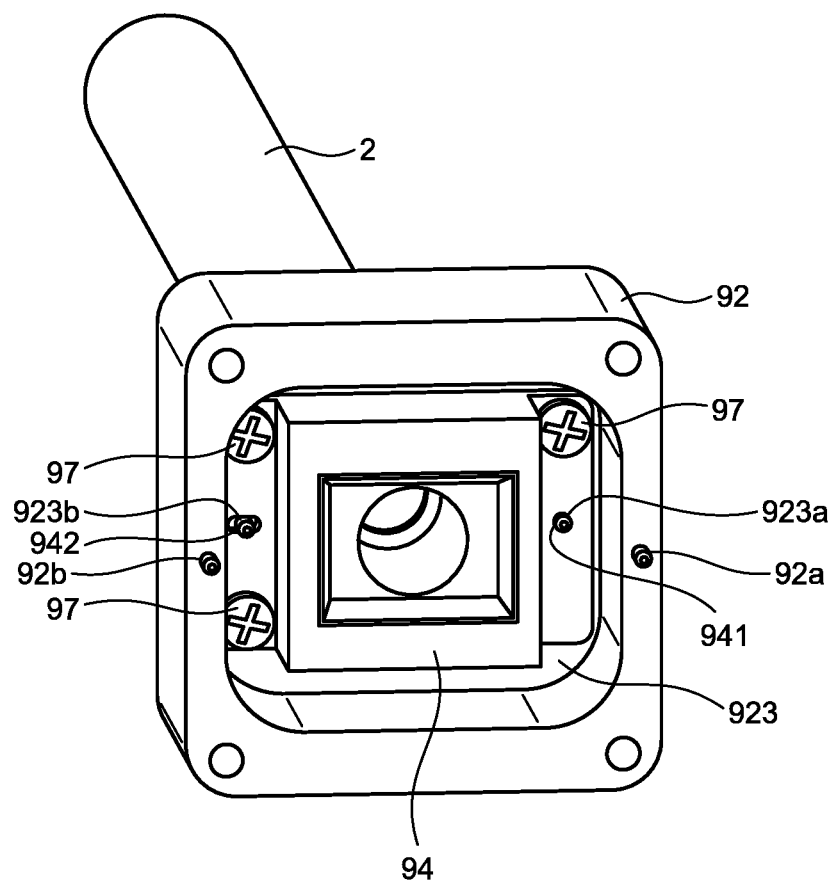
FIG. 7 is a perspective view illustrating the configuration of the main part of the camera head according to one embodiment of the present disclosure.
Figure 8:
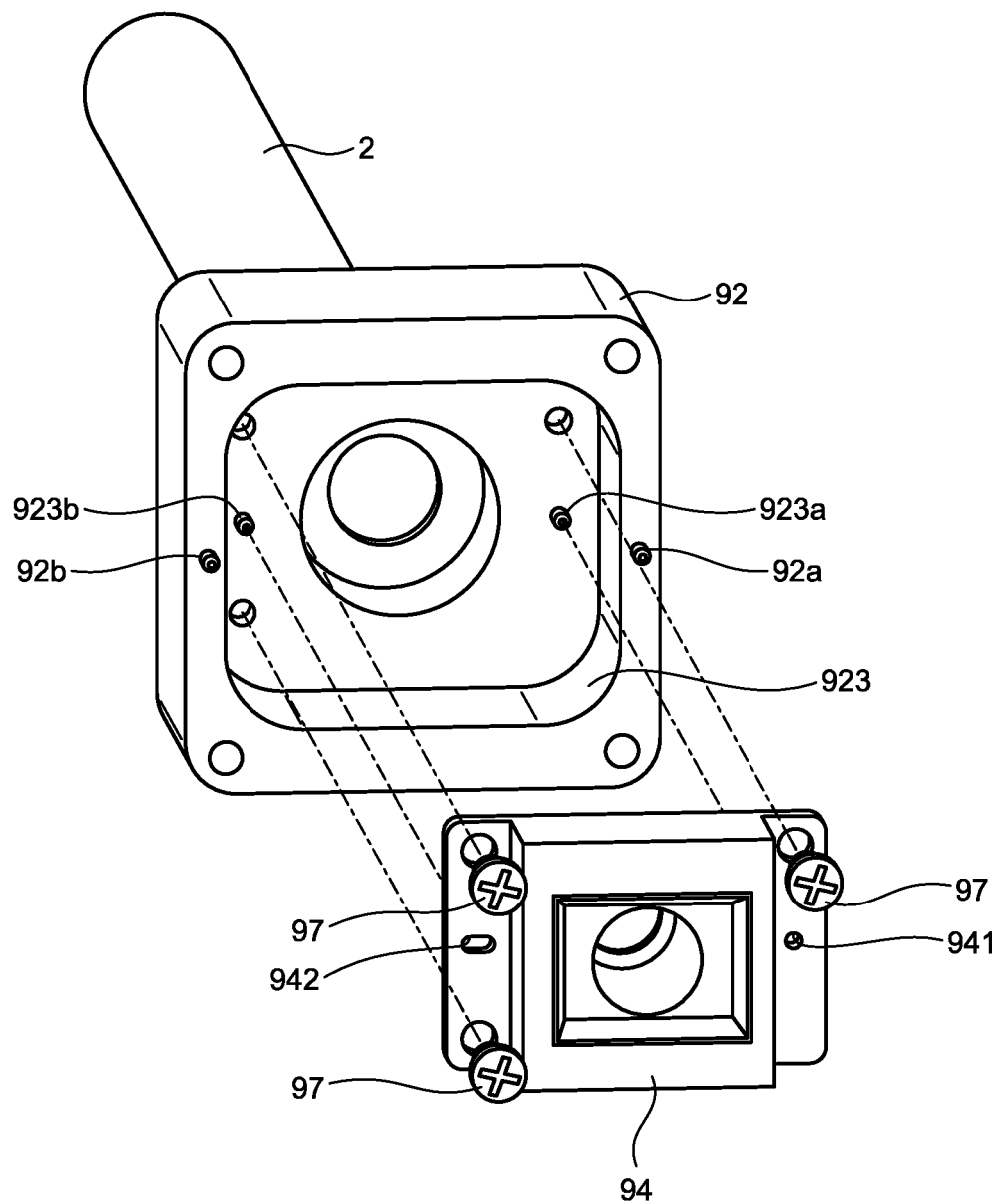
FIG. 8 is an exploded perspective view illustrating the configuration of the main part of the camera head according to one embodiment of the present disclosure.

FIG. 7 is a perspective view illustrating the main part of the camera head according to one embodiment of the present disclosure, and is a diagram illustrating the configuration of the front cabinet unit 92. FIG. 8 is an exploded perspective view illustrating the configuration of the main part of the camera head according to one embodiment of the present disclosure, and is an exploded perspective view of the front cabinet unit 92. Furthermore, in FIGS. 7 and 8, a configuration excluding the pupil modulation filter 921 and the lens unit 922 is illustrated. The endoscope 2 is connected to the front cabinet unit 92, and the pupil modulation filter 921 and the lens unit 922 are retained in the front cabinet unit 92. Specifically, an optical system retaining unit 94 retaining the pupil modulation filter 921 and the lens unit 922 in a direction set in advance, with an interval therebetween, is attached to an attachment unit 923 which is formed in the front cabinet unit 92. Here, in the front cabinet unit 92, positioning pins 923a and 923b formed in the attachment unit 923, are inserted into through holes 941 and 942, and thus, the optical system retaining unit 94 is positioned and is prevented from being rotated. The optical system retaining unit 94, for example, is screwed to the attachment unit 923 by a screw 97 (refer to FIG. 8). Furthermore, the pupil modulation filter 921 and the lens unit 922 may be attached to a portion in which the front cabinet unit 92 and the optical system retaining unit 94 are integrally molded.

The rear cabinet unit 91 and the front cabinet unit 92, for example, are screwed to each other by a screw 95. Here, positioning pins 92a and 92b formed in the front cabinet unit 92, are inserted through hole portions 91a and 91b formed in the rear cabinet unit 91, and thus, the rear cabinet unit 91 and the front cabinet unit 92 are positioned and are prevented from being rotated. Thus, optically accurate adjustment, such as positioning between the imaging unit 911 and the lens unit 922 in a direction along the optical axis, is not performed between the rear cabinet unit 91 and the front cabinet unit 92. The electrical system retaining unit 93 and the optical system retaining unit 94 are separated from each other. Furthermore, the rear cabinet unit 91 and the front cabinet unit 92 may be screwed to each other, and then, abutting portions thereof may firmly adhere to each other by welding.

In the control device 5, the control unit 55 causes the image generating unit 52 to execute image processing according to the connected endoscope 2. Specifically, the control unit 55 causes the image generating unit 52 to perform image generation processing including the restoration processing described above. Accordingly, an image having an enlarged depth of field is generated.

Figure 9:
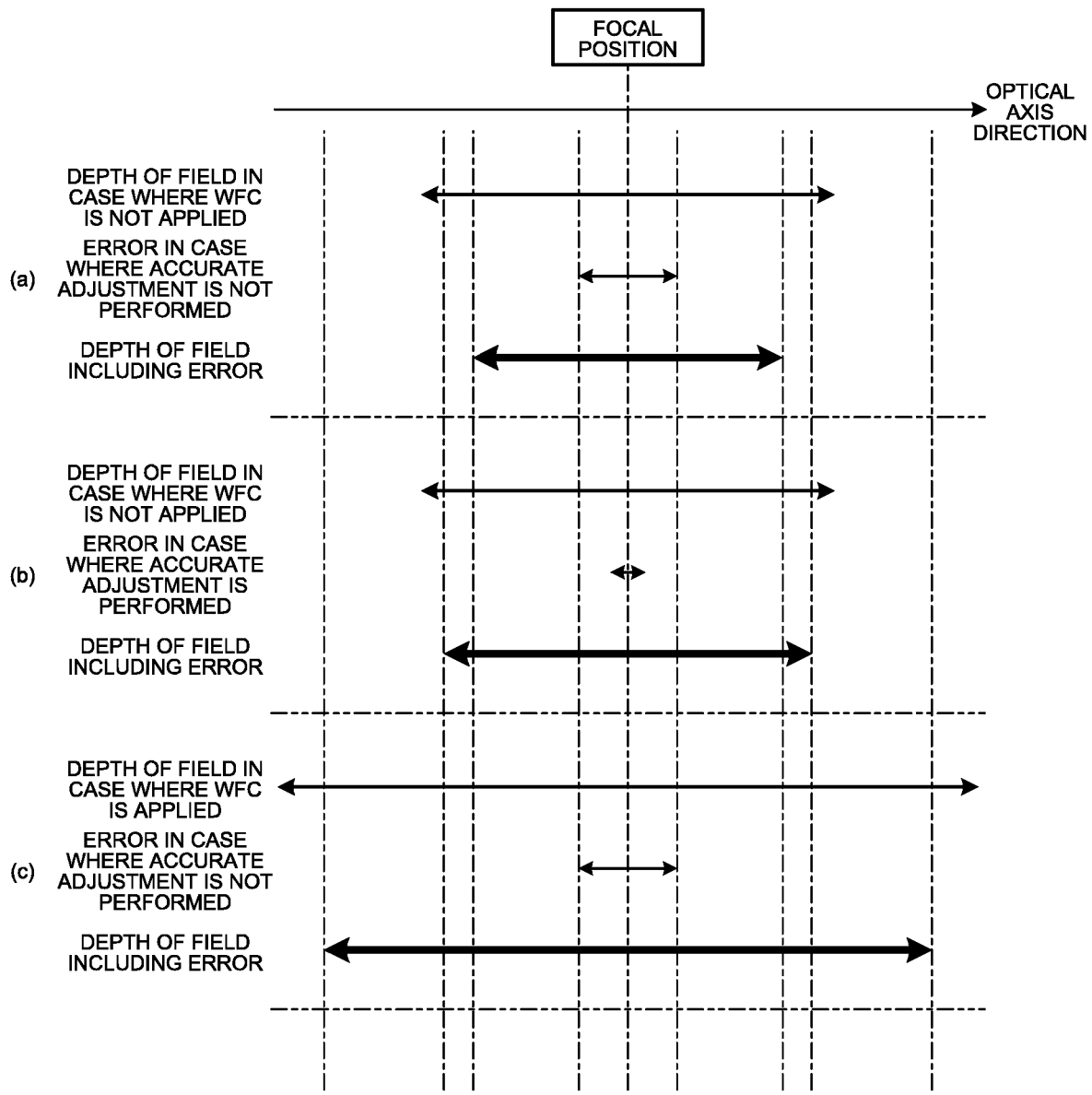
FIG. 9 is a diagram illustrating a depth of field in the camera head according to one embodiment of the present disclosure.

FIG. 9 is a diagram illustrating a depth of field in the camera head according to one embodiment of the present disclosure. In FIG. 9, the camera head is configured of the rear cabinet and the front cabinet, the presence or absence of the pupil modulation filter (the presence or absence of the application of the WFC), and whether or not to perform optically accurate adjustment at the time of connecting the cabinets together are set as a condition, and a depth of field in each condition is illustrated. Part (a) of FIG. 9 illustrates a depth of field in a case where the WFC is not applied, an error in a case where accurate adjustment is not performed, and a depth of field including the error in a case where the WFC is not applied, and the accurate adjustment is not performed. Part (b) of FIG. 9 illustrates a depth of field in a case where the WFC is not applied, an error in a case where the accurate adjustment is performed, and a depth of field including the error in a case where the WFC is not applied, and the accurate adjustment is performed. Part (c) of FIG. 9 illustrates a depth of field in a case where the WFC is applied, an error in a case where the accurate adjustment is not performed, and a depth of field including the error in a case where the WFC is applied, and the accurate adjustment is not performed. The depth of field and the error in FIG. 9, relatively illustrate a range in each of the conditions, by setting a focusing position as a center.

The camera head 9 according to this embodiment has a depth of field illustrated in Part (c) of FIG. 9. As understood from comparison between Part (c) of FIG. 9, and Part (a) and Part (b) of FIG. 9, even in a case where the accurate adjustment is not performed, the depth of field including the error becomes deeper by applying the WFC, compared to the depth of field including the error in a case where the accurate adjustment is performed without applying the WFC.

In the embodiment described above, in the camera head 9 configured by connecting the rear cabinet unit 91 and the front cabinet unit 92 together, the WFC can be applied by providing the pupil modulation filter 921, and thus, even in a case where the rear cabinet unit 91 and the front cabinet unit 92 are connected to each other without performing the accurate adjustment, a depth of field deeper than a depth of field in a case where the accurate adjustment is performed without applying the WFC, is realized. According to this embodiment, even in a case where the casing retaining the optical system, is separated from the casing retaining the image sensor, it is possible to suppress a decrease in a depth of field.

In addition, in the embodiment described above, the configuration of the electrical system is retained in the rear cabinet unit 91, and the configuration of the optical system is retained in the front cabinet unit 92. According to this embodiment, an electrical configuration is completed in the rear cabinet unit 91, and an optical configuration is completed in the front cabinet unit 92, and thus, it is possible to separately handle the optical system and the electrical system from each other, and to repair only a configuration of the same system as that of a target.

Furthermore, in this embodiment, the depth of field of the subject image according to the white illumination light is enlarged by wavefront coding, but an effect using the wavefront coding is not limited thereto. For example, when fluorescent observation is performed by using indocyanine green (ICG), there is a case where infrared light, or white light and infrared light are illuminated in time division. Thus, in lights having different wavelength bands, an optical imaging position is displaced due to the influence of chromatic distortion, and as a result thereof, a phenomenon occurs in which a focusing position is displaced. Thus, even in a case where the optical focusing position is displaced, it is possible to enlarge the depth of field by using the wavefront coding, and to obtain a focused image.

Furthermore, in the embodiment described above, it has been described that the rear cabinet unit 91 and the front cabinet unit 92 are connected to each other by allowing end surfaces to abut on each other, and by inserting the positioning pins 92a and 92b into the hole portions 91a and 91b, but a connection method is not limited thereto. For example, forming units of the positioning pin and the hole portion may be reversed, and the positioning pin and the hole portion may be configured of a groove surrounding the end surface of the unit, and a protrusion fitted into the groove.

MODIFICATION EXAMPLE

Figure 10:
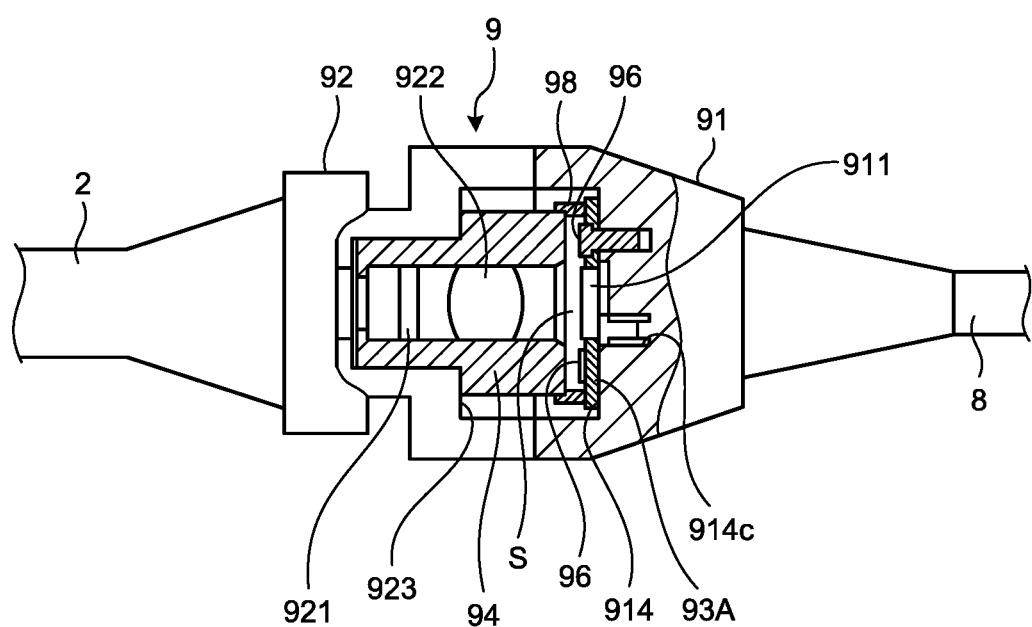
FIG. 10 is a partial sectional view illustrating a configuration of a camera head according to a modification example of the embodiment of the present disclosure.

Subsequently, a modification example of the embodiment of the present disclosure will be described with reference to FIG. 10. FIG. 10 is a partial sectional view illustrating a configuration of a camera head of the modification example of the embodiment of the present disclosure. The same reference numerals will be applied to the same portions as those of the configuration of FIG. 4. In this modification example, a sealing member 98 is provided which is configured of a member having elasticity, in addition to the configuration of the embodiment described above. Moreover, in this modification example, an image sensor configuring the imaging unit 911 is mounted, and an electrical system retaining unit 93A on which the sealing member 98 abuts, is provided, instead of the electrical system retaining unit 93.

The sealing member 98 is in the shape of a tube, covering a space S including light path from the optical system to the imaging unit, and is attached to the camera head 9 in a state of abutting on the optical system retaining unit 94 and the electrical system retaining unit 93A with elasticity. The sealing member 98 is disposed to seal the space S between the optical system and the imaging unit, and thus, it is possible to prevent ambient light, water, or dust from entering the optical system and/or the imaging unit, and to add functions of light shielding, dustproof, waterproof, and moistureproof, without blocking the light path from the optical system to the imaging unit. As described above, the sealing member 98 abuts on the optical system retaining unit 94 and the electrical system retaining unit 93A with elasticity, and the electrical system retaining unit 93A and the optical system retaining unit 94 are in a state of being separated from each other through the sealing member 98, as with the embodiment described above.

Furthermore, in this modification example, the sealing member 98 abuts on the optical system retaining unit 94 and the electrical system retaining unit 93A, but may abut on the optical system retaining unit 94 and the rear cabinet unit 91, may abut on the front cabinet unit 92 and the electrical system retaining unit 93A, and may abut on the front cabinet unit 92 and the rear cabinet unit 91.

The modes for carrying out the present disclosure have been described, but the present disclosure is not limited to the embodiment described above. In the embodiment described above, it has been described that the control device 5 performs signal processing or the like, but the signal processing or the like may be performed on the camera head 9 side.

As described above, even in a case where the casing retaining the optical system is separated from the casing retaining the image sensor, the endoscopic device according to the present disclosure is useful to suppress a decrease in a depth of field.

According to the present disclosure, even in a case where a casing retaining an optical system is separated from a casing retaining an image sensor, it is possible to suppress a decrease in a depth of field.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head for use with a medical observation device, the camera head comprising:
    a front cabinet to be attached to the medical observation device, the front cabinet including an optical system including a front lens and a phase modulation filter which modulates a space distribution of a phase of light, wherein the phase modulation filter is between the medical observation device and the front lens; and
    a rear cabinet detachably connected to the front cabinet, the rear cabinet including a sensor which receives light transmitted through the optical system of the front cabinet, and converts the light into an electrical signal.

2. The camera head according to claim 1, further comprising:
    image processing circuitry configured to generate an image by using the electrical signal generated by the sensor, the image processing circuitry configured to generate the image by performing image processing using a point spread function.

3. The camera head according to claim 1, further comprising
    an optical system mount disposed in the front cabinet that retains the optical system, and an electrical system mount disposed in the rear cabinet that retains the sensor.

4. The camera head according to claim 3,
wherein the optical system mount and the electrical system mount are separated from each other, in a state in which the front cabinet and the rear cabinet are connected to each other.

5. The camera head according to claim 4, further comprising:
a seal covering and sealing a space between the optical system mount and the electrical system mount, in a state in which the front cabinet and the rear cabinet are connected to each other.

6. The camera head according to claim 5,
wherein the seal is between the optical system mount and the electrical system mount, and
the optical system mount and the electrical system mount are separated from each other through the seal, in a state in which the front cabinet and the rear cabinet are connected to each other.

7. The camera head according to claim 3, wherein
the electrical system mount is secured to the rear cabinet to prevent rotation,
the optical system mount is secured to the front cabinet to prevent rotation, and
the front cabinet and the rear cabinet are connected so as to avoid rotating relative to each other when they are connected.

8. The camera head according to claim 7, further comprising:
a first attachment, and
a second attachment,
wherein
the electrical system mount is positioned by the first attachment to avoid rotating with respect to the rear cabinet, and
the optical system mount is positioned by the second attachment to avoid rotating with respect to the front cabinet.

9. The camera head according to claim 8, wherein
at least a part of the first attachment is formed on the rear cabinet, and
at least a part of the second attachment is formed on the front cabinet.

10. The camera head according to claim 1, wherein
the sensor is secured to avoid rotating with respect to the rear cabinet,
the optical system is secured to avoid rotating with respect to the front cabinet, and
the front cabinet and the rear cabinet are connected so as to avoid rotating with each other when they are connected.

11. The camera head according to claim 10, further comprising:
a first attachment, and
a second attachment,
wherein
the sensor is positioned by the first attachment to avoid rotating with respect to the rear cabinet, and
the optical system is positioned by the second attachment to avoid rotating with respect to the front cabinet.

12. The camera head according to claim 11, wherein
at least a part of the first attachment is formed on the rear cabinet, and
at least a part of the second attachment is formed on the front cabinet.

13. A camera head for use with a medical observation device, the camera head comprising:
a front cabinet to be attached to the medical observation device, the front cabinet including an optical system and a phase modulation filter which modulates a space distribution of a phase of light;
a rear cabinet detachably connected to the front cabinet, the rear cabinet including a sensor which receives light transmitted through the optical system of the front cabinet, and converts the light into an electrical signal;
an optical system mount disposed in the front cabinet that retains the optical system;
an electrical system mount disposed in the rear cabinet that retains the sensor, wherein the optical system mount and the electrical system mount are separated from each other, in a state in which the front cabinet and the rear cabinet are connected to each other; and
a seal covering and sealing a space between the optical system mount and the electrical system mount, in the state in which the front cabinet and the rear cabinet are connected to each other.

14. The camera head according to claim 13, further comprising:
image processing circuitry configured to generate an image by using the electrical signal generated by the sensor, the image processing circuitry configured to generate the image by performing image processing using a point spread function.

15. The camera head according to claim 13,
wherein the seal is between the optical system mount and the electrical system mount, and
the optical system mount and the electrical system mount are separated from each other through the seal, in a state in which the front cabinet and the rear cabinet are connected to each other.

16. The camera head according to claim 13, wherein
the electrical system mount is secured to the rear cabinet to prevent rotation,
the optical system mount is secured to the front cabinet to prevent rotation, and
the front cabinet and the rear cabinet are connected so as to avoid rotating relative to each other when they are connected.

17. The camera head according to claim 16, further comprising:
a first attachment, and
a second attachment,
wherein
the electrical system mount is positioned by the first attachment to avoid rotating with respect to the rear cabinet, and
the optical system mount is positioned by the second attachment to avoid rotating with respect to the front cabinet.

18. The camera head according to claim 17, wherein
at least a part of the first attachment is formed on the rear cabinet, and
at least a part of the second attachment is formed on the front cabinet.

19. The camera head according to claim 13, wherein
the sensor is secured to avoid rotating with respect to the rear cabinet,
the optical system is secured to avoid rotating with respect to the front cabinet, and
the front cabinet and the rear cabinet are connected so as to avoid rotating with each other when they are connected.

20. The camera head according to claim 13, further comprising:
a first attachment, and
a second attachment,
wherein
the sensor is positioned by the first attachment to avoid rotating with respect to the rear cabinet, and
the optical system is positioned by the second attachment to avoid rotating with respect to the front cabinet.

21. The camera head according to claim 20, wherein
at least a part of the first attachment is formed on the rear cabinet, and
at least a part of the second attachment is formed on the front cabinet.

* * * * *